United States Patent [19]

Lezdey et al.

[11] Patent Number: 5,290,762

[45] Date of Patent: * Mar. 1, 1994

[54] TREATMENT OF INFLAMMATION

[76] Inventors: John Lezdey, 976 Kingston Dr., Cherry Hill, N.J. 08034; Allan Wachter, 9822 S. Grandview, Tempe, Ariz. 85284

[*] Notice: The portion of the term of this patent subsequent to Jun. 8, 2010 has been disclaimed.

[21] Appl. No.: 18,888

[22] Filed: Feb. 17, 1993

Related U.S. Application Data

[63] Continuation-in-part of Ser. No. 781,003, Oct. 18, 1991, Pat. No. 5,217,951, which is a continuation-in-part of Ser. No. 643,727, Jan. 18, 1991, abandoned, which is a continuation-in-part of Ser. No. 598,241, Oct. 16, 1990, abandoned, and a continuation-in-part of Ser. No. 591,630, Oct. 2, 1990, Pat. No. 5,008,242, which is a continuation-in-part of Ser. No. 445,005, Dec. 4, 1989, which is a continuation-in-part of Ser. No. 242,735, Sep. 9, 1988, abandoned, and a continuation-in-part of Ser. No. 181,707, Sep. 8, 1988, Pat. No. 4,916,117, which is a continuation-in-part of Ser. No. 946,445, Dec. 24, 1986, abandoned.

[51] Int. Cl.$^5$ .............................................. A61K 37/64
[52] U.S. Cl. ........................................ 514/8; 514/2; 514/12; 514/21
[58] Field of Search ........................ 514/8, 2, 21, 12

[56] References Cited

U.S. PATENT DOCUMENTS 5,217,951 6/1993 Lezdey et al. ........................ 514/8

Primary Examiner—Howard E. Schain
Assistant Examiner—Choon P. Koh
Attorney, Agent, or Firm—John Lezdey

[57] ABSTRACT

A method for the prophylaxis or direct treatment of inflammatory diseases or injuries in a patient which comprises administering to the site of the disease or injury an effective amount of at least one serine protease inhibitor, its salts, derivatives or analogs which bind with the mast cell mediators, T-cell mediators or kallikrein.

16 Claims, No Drawings

TREATMENT OF INFLAMMATION

RELATED APPLICATION

This application is a continuation-in-part of application Ser. No. 781,003 filed Oct. 18, 1991, now U.S. Pat. No. 5,217,951, which is a continuation-in-part of application Ser. No. 643,727 filed Jan. 18, 1991, now abandoned, which is a continuation-in-part of application Ser. No. 598,241 filed Oct. 16, 1990, now abandoned, and application Ser. No. 591,630 filed Oct. 2, 1990, now U.S. Pat. No. 5,008,242 which is a continuation-in-part of application Ser. No. 445,005 filed Dec. 4, 1989, which is a continuation-in-part of application Ser. No. 242,735 filed Sep. 9, 1988, now abandoned, and application Ser. No. 181,707 filed Sep. 8, 1988, now U.S. Pat. No. 4,916,117, which are continuations-in-part of application Ser. No. 946,445 filed Dec. 24, 1986, now abandoned.

FIELD OF THE INVENTION

The present invention relates to a method and composition for treating mammals afflicted with inflammatory diseases or injuries. More particularly, the present invention relates to the treatment of certain inflammatory conditions in patients, by administering serine protease inhibitors, their analogs, salts or derivatives. There is particularly provided topical compositions for treating the symptoms of inflammatory skin conditions. The inhibitors bind with mast cell and/or T-cell mediators and/or kinins.

BACKGROUND OF THE INVENTION

Prior to the present invention it was generally believed that serine protease inhibitors could be used only to supplement a deficiency occurring as a result of a genetic defect or a chemically produced deficiency resulting from an event such as smoking. Moreover, no consideration was previously given for directly controlling diseases in which mast cells are implicated by administering serine protease inhibitors when serum levels of proteases or protease inhibitors are normal. Mast cells have been found to be implicated in diseases and events such as allergic and non-allergic rhinitis, nasal polyposis, atopic dermatitis, including psoriasis, contact dermatitis, pancreatitis, emphysema, asthma, colitis, Crohn's Disease, wound healing, cluster headaches, coronary artery spasm, etc.

The role of mast cells in humans is the same as in animals. addition, animals contain counterparts to human $\alpha$-1-antichymotrypsin, $\alpha$-1-antitrypsin, and other serine protease inhibitors. In fact, it has been shown that human $\alpha$-1-antitrypsin will bind with animal mast cells and the mediators derived therefrom.

Inflammation is a non-specific response of tissues to diverse stimuli or insults and results in release of a variety of materials at the site of inflammation that induce pain. It is now recognized that mast cells are implicated in the pathophysiology of inflammatory skin conditions as well as in other physiological disorders. Mast cells provide the greatest source of histamines in acute inflammation. Basophils are another source. Mast cells have also been noted in hypertrophic scars.

Eosinophils, basophils and neutrophils are prominent in inflammatory lesions due to the potent chemoattractants released. Neutrophils are a main source of serine elastase and cathepsin G which are important in the tissue damage resulting from inflammation.

Kallikreins and kinins are recognized as being associated with defense and repair responses in mammals. However, excess kallikreins and kinins can cause pain and tissue damage.

The most direct approach to therapy of inflammatory skin conditions appears to be a direct attack at the site of inflammation of the mediators of inflammation and pain and the reduction of those neutrophilic derivatives which can cause damage to the growth of new tissue during the healing process.

It is understood that the term "serine protease inhibitors" as used herein refers to the inhibitors derived from a human source and the corresponding recombinant product which is either glycosylated or non-glycosylated.

SUMMARY OF THE INVENTION

The present invention relates to a method for treating non-bronchial inflammatory conditions in patients by the administration of serine protease inhibitors selected from the group consisting of secretory leucocyte protease inhibitor, C-reactive protein, serum amyloid A protein, alpha 2-macroglobulin, alpha 2-antiplasmin, their analogs, salts or derivatives which alone or in combination with one or more other serine protease inhibitors which have a specific activity for mast cell mediators or the proteases derived therefrom, for example such as cathepsin-G, elastase, kinins or their precursors, in a suitable pharmaceutical composition.

Serine protease inhibitors have been found to play a major role in the direct inactivation of the mediators of inflammation so that the normal wound healing process can be accelerated without interference from the excess of materials released at the site of inflammation. The almost immediate disappearance of pain and itch indicates that there can be a control of the kinins as well. A cocktail of serine protease inhibitors would therefore be useful to deactivate those mediators of inflammation which may not yet be recognized or are found in association with a particular disease.

As presently found, serine protease inhibitors are useful in the treatment of burn patients which not only experience pain and itch but have a problem in controlling the laydown of organized collagen because of elastase and cathepsin G; serine protease inhibitors permit the rapid growth of normal skin.

The administration of serine protease inhibitors appears to be a viable alternative to the administration of steroids to reduce inflammation and to treat inflammatory skin conditions not treatable with steroids or reduce the steroid requirement.

It has now been found that controlling the amount of the destructive enzymes at the site of inflammation can prevent proliferation of the disease, prevent associated tissue damage and promote healing. It has also been found that the administration of serine protease inhibitors which inactivate destructive proteases alone provide a major control of the symptoms of the disease. However, since the cause of disease may be a result of more than one factors, the use of more than one protease inhibitor provides a better chance of success for early remission of the symptoms and for a prophylactic control of the symptoms associated with the disease. Serine protease inhibitors, for example, alpha 2-macroglobulin and C-reactive protein (CRP), when administered to the site of inflammation provides a reduction in swelling, pain and stiffness.

For chronic cases of dermatitis, a cocktail of protease inhibitors is preferably administered at the site of inflammation. The treatment can be simultaneous with or followed with the addition of an appropriate steroid or antibiotic.

The serine protease inhibitors provide their anti-inflammatory action which applied under the law of mass action. That is, while protease inhibitors are normally found in diseased states as a result of the functioning of bodily organs, namely, the liver, it is only when a mass or a larger than normal amount of the inhibitors is applied at the site of inflammation that equilibrium between mediators and inhibitors is changed so as to produce an immediate action and provide an anti-inflammatory effect. Alpha 2-macroglobulin also provides an inhibitory action against parasite invasion.

The serine protease inhibitors which are contemplated in the present invention are any of the inhibitors, their analogs, derivatives or salts which can inhibit mast cell mediators or bind with any one or more of the protease derived from eosinophils, basophils and/or neutrophils such as elastase, cathepsin-G, tryptase, chymase, kinins, kalikrein, tumor necrosis factor, chymotrypsin, collagenase, and the like.

The serine protease inhibitors included in the present invention are alpha 2-macroglobulin, alpha 2-antiplasmin, C-reactive protein, beta 1-antigellagenase, serine amyloid A protein, alpha cysteine protease inhibitors, inter-alpha-trypsin inhibitor, secretory leucocyte protease inhibitor, bronchial mucous inhibitor, and C-1-inhibitor (an inhibitor of plasma kallikrein). The inhibitors of the invention may be natural or prepared by recombinant means.

Alpha 2-antiplasmin is a single-chain glycoprotein containing 11% carbohydrate, and asparagine and leucine as the amino terminal residues. This enzyme has a molecular weight of about 65,000 to 70,000. This inhibitor can inactivate kallikrein, chymotrypsin ($Kass=1.0\times10^5 M^{-1} sec^{-1}$), plasmin, Factor Xa and Factor XIa.

Alpha 2-macroglobulin is a 720 KD acute-phase serum glycoprotein that is synthesized in the liver and can be obtained by gel filtration chromatography. It can irreversibly bind with most proteases and complements C3 and C5 so as to stop the inflammation cascade when applied in excess to the site of inflammation.

Alpha 2-macroglobulin have been especially useful in the treatment of the various inflammatory skin conditions including those which are induced by autoimmune disease, virus and bacterial infections. This inhibitor has also been found to cause vasoconstriction, which in inflammation, decreases swelling and redness and to eliminate pain and itching.

Alpha 2-macroglobulin has also been found especially useful in the treatment of topical inflammatory conditions because it comprises similar active sites as alpha 1-antitrypsin and alpha 1-antichymotrypsin. Alpha 2-macroglobulin contains an active site which inhibits glycosylation enhancing factor (GEF) from T-cells so as to prevent degranulation of masts cells by IgE and binds with basophils to inhibit histamine release. It is also useful for treating optic and otic inflammations.

Alpha 2-macroglobulin alone or in combination with a corticosteriod controls the release of histamine releasing factors and binds with interleukin-1 beta.

It has also been found that alpha 2-macroglobulin through the sialic acids of the N-linked carbohydrate (oligosaccharide) groups bind to viral hemagglutinins. This binding action inhibits viral absorption and infection by such viruses as the influenza virus. Therefore viral inflammation in some cases can be controlled.

Furthermore, alpha 2-macroglobulin when administered to a site of high trypsin activation forms a complex which plays a role in phagocytosis of group A and C streptococci.

The drugs of the invention may be prepared by cloning, by conventional techniques utilizing an oligonucleotide probe or antibody probe, and the like. The recombinant gene product of the invention is especially useful since it is free of contaminating viruses when produced.

The analogs, salts and derivatives may be formed utilizing conventional techniques associated with other proteins without effecting the utility of the compound. There may be prepared the alkali metal salts, acid-addition salts, and esters similar to other proteins or peptides.

Some inflammation conditions are not immediately identifiable as to source and the factors which are involved to produce the different symptoms are not readily apparent. Therefore, it is desirable to administer in some case a combination or cocktail of serine protease inhibitors to provide a broad spectrum of drugs which can provide rapid relief of the different symptoms of inflammation. The most effective combination is alpha 2-macroglobulin with a protease inhibitor that is specific for the mass of mediators present. Preferably, the combination is administered in a ratio of 1:1:1: to 3:2:1: either in a single unit or in separate dosage form.

When topically applied such as in an aqueous medium, a serine protease inhibitor such as alpha 2-macroglobulin in suitable composition form is useful in the treatment of burns and inflammatory skin diseases such as psoriasis, eczema, viral inflammations, protecting middle ear mucosa against proteolytic damage and the like. It has been demonstrated that treatment with alpha 2-macroglobulin together with $\alpha$1-antitrypsin has reduced pain when applied to skin lesions.

The use of a non-aqueous lipid miscible carrier, for example, such as prepared with liposomes are particularly advantageous since they provided improved activity at the treatment sites.

It is therefore an object of the invention to provide an anti-inflammatory composition which can relieve the swelling and redness associated with inflammatory conditions in humans and animals.

It is a further object of the invention to provide an anti-inflammatory composition which is well tolerated by the human body and is free of side effects, and for its counterparts for animal use.

It is a yet still further object of the invention to provide a method and a composition for treating inflammatory skin conditions.

DETAILED DESCRIPTION OF THE PRESENT INVENTION

The objects of the present invention can be achieved by the administration of serine protease inhibitors alone or in combination in a suitable pharmaceutical form to patients suffering from inflammatory conditions.

The present invention provides a pharmaceutical composition which comprises a compound of this invention and a pharmaceutically acceptable carrier. The compound may be used alone or in combination with other serine protease inhibitors to provide a broad spectrum of treatment.

In the treatment of burns, a 20% solution of a serine protease inhibitor such as alpha 2-macroglobulin, alone or in combination with other serine protease inhibitors, in sterile water or saline solution, may be sprayed on the patient or the burn area may be wrapped in wet bandages. A wound healing or skin growth factor may be included. The treatment provides immediate relief of pain. The patient may then be treated with the solution daily until the healing process is normal. Depending upon the severity of the burns, the patient may be further treated with other medications to prevent infection.

The following examples further illustrate the practice of this invention, but are not intended to be limiting thereof. It will be appreciated that the selection of actual amounts of specific serine protease inhibitors to be administered to any individual patient (human or animal) will fall within the discretion of the attending physician and will be prescribed in a manner commensurate with the appropriate dosages will depend on the stage of the disease and like factors uniquely within the purview of the attending physician.

EXAMPLE I

A topical cream was prepared as follows:

| A. The following mixture was prepared: | |
| --- | --- |
| alpha 2-macroglobulin | 1.0 g |
| Olive oil | 5.0 g |
| Cetanol | 2.0 g |
| Stearic acid | 5.0 g |
| Glycerin aliphatic acid ester | 12.0 g |
| Tween 60 | 0.5 g |
| B. The following mixture was also prepared: | |
| Propylene glycol | 0.5 g |
| Methyl paraben | 0.1 g |
| Propyl paraben | 0.02 g |
| Purified water to | 100 g in total |

The mixture of parts A and B were blended together by conventional means to give a total of 100 g. of 100% by weight topical cream which could be utilized for treatment of inflammatory dermatological conditions. If desired secretory leucocyte protease inhibitor and/or alpha 1-antitrypsin may be added in an amount of 1.0 g to part A.

EXAMPLE II

An oleaginous anhydrous ointment was prepared with the following composition:

| Composition | % |
| --- | --- |
| alpha 2-macroglobulin | 1.0 |
| Soy phosphatide | 4.0 |
| Plastibase 50W | 94.975 |
| Butylated hydroxytoluene | 0.025 |
| | 100.00 |

Other non-aqueous lipid miscible carriers may also be utilized. However, it is understood that other serine protease inhibitors can also be similarly formulated.

EXAMPLE III 1000 mg of alpha 2-macroglobulin can be dissolved in 50 ml of saline solution so as to treat a patient suffering from swelling and open lesions of the hand by immersing the hand in the solution. Pain generally disappears within 6–10 minutes of treatment. Treatment should be continued for 1 hour.

A similar composition can be utilized as an otic wash for dogs with ear infections followed by the administration of a steroid.

EXAMPLE IV

A suitable cream for topical use is prepared by admixing 58 g of alpha 2-macroglobulin with 6 ml of water and 1000 g of a balm available under the trademark AQUAPHOR, sold by Beiesdorf Inc., Norwalk, Conn. AQUAPHOR comprises a mixture of petrolatum, minerial oil, wax and wool wax alcohol.

The cream is useful for minor irritations and in the treatment of inflammatory skin conditions.

EXAMPLE V

In the treatment of colitis a 20% solution of alpha 2-macroglobulin may be prepared and administered as an enema.

A similar result will be found with an secretory leucocyte protease inhibitor.

We claim:

1. A method for the treatment of inflammatory diseases or injury in mammals which comprises administering to the site of the disease or injury an effective amount of at least one natural or recombinant serine protease inhibitor selected from the group consisting of secretory leucocyte protease inhibitor, C-reactive protein, serum amyloid A protein, alpha 2-macroglobulin, alpha 2-antiplasmin, its analog, salt or derivative which has an affinity to a mast cell mediator, plasma kinins or a T-cell mediator.

2. The method of claim 1 including the administration of a mixture of serine proteases inhibitors.

3. The method of claim wherein said serine protease inhibitor is alpha 2-macroglobulin.

4. The method of claim 1 wherein said inflammatory disease is dermatological.

5. The method of claim 4 wherein said inflammatory disease is psoriasis.

6. The method of claim 1 wherein said inflammatory disease is optic or otic.

7. The method of claim 1 wherein said patient is an animal.

8. The method of claim 1 wherein said patient is human.

9. The method of claim 1 wherein said mediators comprise neutrophils, basophils or eosinophils.

10. The method of claim 1 wherein said mediators comprise cathepsin G and elastase.

11. The method of claim 1 wherein said mediators comprise kinins.

12. The method of claim 1 wherein said serine protease inhibitor is secretory leucocyte protease inhibitor and the mast cell disease is dermatitis.

13. The method of claim 1 wherein said patient has an elevated IgE level.

14. A method for inhibiting histamine release in a patient suffering from a mast cell implicated disease which comprises administering to said patient an effective amount of alpha 2-macroglobulin.

15. A pharmaceutical composition for treatment of a mast cell implicated disease in mammals comprising an effective amount of at least one natural or recombinant serine protease inhibitor selected from the group consisting of secretory leucocyte protease inhibitor, C-reactive protein, serum amyloid A protein, alpha 2-macroglobulin, alpha 2-antiplasmin, its analog, salt or derivative which has an affinity to a mast cell mediator, plasma kinins or a T-cell mediator, and a pharmaceutically acceptable carrier.

16. A pharmaceutical composition for treating viral diseases affecting a mammal which comprises an antivirally effective amount of alpha 2-macroglobulin and a pharmaceutically acceptable carrier.

* * * * *